United States Patent [19]

Barak

[11] Patent Number: 5,169,866
[45] Date of Patent: Dec. 8, 1992

[54] METHOD FOR CONTROLLING MICROORGANISMS ON POTATOES

[75] Inventor: Ayala Barak, Jerusalem, Israel
[73] Assignee: Bromine Compounds Limited, Israel
[21] Appl. No.: 713,568
[22] Filed: Jun. 11, 1991

[30] Foreign Application Priority Data

Oct. 17, 1988 [IL] Israel .................................. 88066

[51] Int. Cl.$^5$ .............................................. A01N 37/34
[52] U.S. Cl. ...................................... 514/528; 514/957
[58] Field of Search ................................ 514/528, 957

[56] References Cited

U.S. PATENT DOCUMENTS

| | | | |
|---|---|---|---|
| 3,733,332 | 5/1973 | Toepfl et al. .................... | 260/293.86 |
| 4,173,651 | 11/1979 | Muramoto et al. .................. | 424/306 |
| 4,292,322 | 9/1981 | Muramoto et al. .................. | 424/274 |
| 4,761,427 | 8/1988 | Segall et al. .......................... | 514/528 |
| 4,866,094 | 9/1989 | Barak ................................... | 514/528 |

OTHER PUBLICATIONS

Law et al., *Transactions of the ASAE*, 9(4), 501–6 (1966).

Primary Examiner—Allen J. Robinson
Attorney, Agent, or Firm—Lerner, David, Littenberg, Krumholz & Mentlik

[57] ABSTRACT

Seed potatoes are fogged with a composition comprising 2,2-dibromo-3-nitrilopropionamide. Control of pathogens on potatoes is obtained with relatively low amounts of active material.

5 Claims, No Drawings

METHOD FOR CONTROLLING MICROORGANISMS ON POTATOES

This is a continuation-in-part of application Ser. No. 07/417,568 filed Oct. 5, 1989, abandoned.

BACKGROUND OF THE INVENTION

The present invention relates to a method for controlling microorganisms, particularly fungi and bacteria on potato tubers. More particularly, the invention relates to a method employing 2,2-dibromo-3-nitrilopropionamide (DBNPA) as the active ingredient, and in which the tubers or the seed tubers to be treated are fogged therewith.

DBNPA is a well-known biocide, useful in a number of industrial and agricultural applications. In a patent application of the same applicant there is described a method for controlling microorganisms on potato tubers and potato seeds, by the fumigation of DBNPA, which provides microorganism control with high effectiveness. Fogging of DBNPA on potato seeds, which is the subject matter of the present invention, however, has never been attempted. Fogging typically involves the suspension in air of liquid droplets from about 0.1 to about 30 microns in diameter. The mean diameter of the droplets within this range is usually from about 0.5 to about 4.0 microns, although other mean diameters of the 0.1 to 30 micron particles are also suitable for use with the present invention. Fogging differs from fumigation, which is carried out by substantially evaporating the compound involved. By conventional definition, evaporation requires a change of state from liquid to gas. Fumigation, therefore, mixes gas-phase molecules of DBNPA with air. The gas-phase molecules of DBNPA are significantly smaller than the liquid droplets of DBNPA suspended in the air by fogging.

Biocide application is often carried out by spraying. Spraying, however, differs from fogging in that it involves droplet sizes in the order of magnitude of 80-90 microns. When a biocide is applied by spraying, a large quantity - half or more - of the droplets reach the walls and the floor of the spraying chamber. Thus, the effective amount of biocide is relatively low, and relatively high total amounts of biocides are therefore required, which is a considerable drawback, especially from the economic, health and environmental point of view.

SUMMARY OF THE INVENTION

It has now been found, and this is an object of the present invention, that it is possible effectively to control various fungi and bacteria on potato seeds and tubers, by fogging them with relatively low amounts of DBNPA, if the active material is properly applied. Thus, according to the invention, a typical amount of material employed is about 0.6-1.2 liters of a 20% DBNPA liquid formulation, for each ton of seed tubers, which is a very low amount, as will be apparent to a person skilled in the art.

The method for controlling the growth of microorganisms on seed tubers, according to the invention, comprises fogging the potato tubers in a fogging chamber with a composition comprising 2,2-dibromo-3-nitrilopropionamide.

According to a preferred embodiment of the invention, the composition comprises between 10% and 30% by weight of 2,2-dibromo-3-nitrilopropionamide, between 40% to 70% dipropylene glycol (DPG) and between 10% and 30% of water.

Preferably, the ratio between the empty and occupied volume of the fogging chamber is comprised between substantially zero (chamber completely full) and 1 (chamber half full), and still preferably, the amount of 2,2-dibromo-3-nitrilopropionamide employed for each ton of tubers stored in the fogging chamber is comprised between 0.6 to 1.2 liter of a 20% formulation per ton of tubers. As will be apparent to a person skilled in the art, the amounts indicated herein refer to substantially sealed fogging chambers, viz., to fogging chambers which receive and utilize most of the fogged material and in which no substantial escape of fogged material is permitted. In situations in which appreciable amounts of fogged material escape the fogging chambers, higher amounts need be employed.

Fogging is the application of fog droplets with a fogger. As noted above, fog droplets are understood by those of ordinary skill in the art as being liquid droplets suspended in air. Perry and Chilton, *Chemical Engineers' Handbook*, (Fifth Ed., McGraw-Hill, New York), pp. 18-66, describe the particle size of fog droplets as being between 0.1 and 30 microns. This definition is hereby incorporated herein by reference thereto.

The mean diameter of fog droplets within a 0.1 and 30 micron range may vary and those of ordinary skill in the art will understand what mean diameters of fog droplets are suitable for use with the present invention. A mean droplet diameter between about 0.5 and about 4.0 microns is preferred. By conventional definition, a sample of fog droplets can have a mean diameter between about 0.5 and about 4.0 microns and at the same time range in particle size between 0.1 and 30 microns.

While any convenient fogger which provides the appropriate droplet size can be employed, using a thermal fogger has been found to be convenient. When a thermal fogger is employed, however, it is desirable to avoid long exposures of the biocide to high temperatures, to avoid deterioration due to decomposition.

As will be seen from the following description, fogging is not only a convenient way of applying DBNPA to the tubers, but, if carried out properly, as herein described, fogging provides pathogen control which is superior to that of the closest method, viz., Ultra Low Volume Spraying, although surprisingly lower amounts of active material are required in the method of the invention, as compared to spraying.

DETAILED DESCRIPTION OF THE INVENTION

The above characteristic and advantages of the invention will be better understood through the following illustrative and nonlimitative description of preferred embodiments, and comparative examples.

EXAMPLE 1

Fogging of Seed Potato Tubers

Inoculated seed tubers (Famosa), infected with Spongaspora sp. and Erwinia sp. ($3.0 \times 10^6$ cfu/tuber) were treated with DBNPA immediately after harvesting and prior to storing. Three sacks of these seed tubers were placed in a 40 m$^3$ storage room, at room temperature. A fogger was charged with a formulation containing 20% DBNPA, 60% DPG and 20% H$_2$O, by weight. The fogger used was a thermal fogger (IGEBA TF-30). The tank and all connecting pipes were made of stainless steel and the operating pressure reached up to 2 atm. The hot air temperature was 80° C. The biocidal solution was injected into the hot air at the end of the pipe, so that contact time of the biocide with air at elevated temperature was minimal. The flow control jets were adjusted to 20 l/h (the tank may contain up to 6 liters of solution). Fogging was also attempted at higher hot air temperatures (up to 300° C.), and no severe decomposition of the active ingredient was revealed from the analysis of the fogged active ingredient, probably due to the short contact time. The cooling ventilation system of the storage room started operating only at the beginning of the fogging. The storage room was sealed and the fogger was connected through an opening in the ventilation system. The fogger operated for 15 minutes, during which 2.2 lit. of the formulation were fogged. The storage chamber was left closed for two weeks, after which the seed tubers were taken out and examined for residual microorganisms and biocide. No residual biocide was found on the fogged tubers. Total viable count was reduced by 2 orders of magnitude: Erwinia sp. was reduced by 2 orders of magnitude, and fungi were reduced by two and a half orders of magnitude. The results are shown in Table I below. Samples taken from the outside part and the inside of the potato sack did not show any appreciable difference, when pathogens were assayed.

"Fogging in" designates a fogging treatment effected at the beginning of storage; "fogging out" designates a treatment effected at the end of the storage period, and "fogging in and out" a treatment effected at both times.

From Table I it can be appreciated, by comparing the results for the fogged tubers with those for the control, that appreciable control is obtained for all species, and total control is obtained in most cases for fungi.

The seed tubers so treated were planted in September 1987 in Gilat, Maon, and were recovered from the field at the end of January, 1988. The extent of powdery scab on Famosa daughter potato tubers was determined, and the results are set forth in Table II.

EXAMPLE 2 (COMPARATIVE)

Ultra-Low Volume Spraying

Ultra-low volume spraying experiments were carried out as a means to evaluate the efficacy of fogging. Seed potato tubers from the same lot used in Example 1 were sprayed in a disinfecting chamber, using the following solutions:

(a) a 1:1 dilution of a 20% DBNPA, 60% DPG, 20% $H_2O$ and 0.1% nonylphenylethoxylate (NP-10) solution, with tap water.

(b) 20% DBNPA, 60% DPG, 20% $H_2O$ and 0.1% NP-10 solution.

The results are detailed in Table III below. As it can be appreciated from the comparison of Tables I and III, Ultra Low Volume Spraying is substantially inferior to fogging, and results in substantially less control of potato tuber pathogens. This result is surprising in view of the close similarity of the two methods of application.

EXAMPLE 3

Kara potato tubers were fogged in four small unsealed storage cells, having a total volume of 1180 liter each. In Cell No. 1, 40 kg of seed potato tubers were fogged with 17 ml of 20% DBNPA solution in 60% DPG and 20% water; in Cell No. 2, 40 kg of seed potato tubers were fogged with 50 ml of the same solution. In Cell No. 3, 40 kg of seed potato tubers were fogged with 37 ml of the same solution, and in Cell No. 4, 80 kg of seed potato tubers were fogged with 37 ml of the same solution. Because the storage cells were unsealed, only an estimated 0.25 ml solution/kg tuber did not escape out of the cell. The results are detailed in Table IV and show that even under such unfavorable conditions control is obtained.

EXAMPLE 4

Two different types of potato tubers, namely Desiree originating from Scotland and Desiree originating from Holland, were fogged in a 40 $m^3$ storage room. A sack of each type was added to additional 15 tons of seed potato tubers contained in the storage room. The room was fogged with 12 lit of a 20% solution of DNBPA in 60% DPG and 20% water during 35 minutes, giving a 0.8 lit/ton of fogged solution. Seed potato tubers were removed from the storage room after 4 weeks, and examined for residual pathogens. The results are set forth in Table V below.

As is apparent from the above description and examples, the method of the invention is simple, economic and effective. Many variations can be effected in the method of the invention. Different fogging equipment can be employed, for instance, or different DBNPA formulations can be used, without exceeding the scope of the invention.

TABLE I

| Treatment | total* fungi | Rh* | Py* | Fu* | Ve* | Ecc* | Eca* | Res |
|---|---|---|---|---|---|---|---|---|
| None (control) | $4.1 \times 10^4$ | 17 | 180 | $7 \times 10^3$ | 4 | $3 \times 10^5$ | $4.7 \times 10^5$ | 0 |
| Fogging in | $1.5 \times 10^2$ | 0 | 0 | $6 \times 10^2$ | 0 | $2.5 \times 10^2$ | $1 \times 10^3$ | $<10^{-4}$ |
| Fogging Out | $2.1 \times 10$ | 0 | 0 | 0 | 0 | 40 | 80 | $<2 \times 10^{-7}$ |
| Fogging In & Out | $3 \times 10$ | 0 | 0 | 0 | 0 | 80 | 10 | $<2 \times 10^{-7}$ |

*cfu/tuber
Rh = Rhizoctonia Solani
Py = Pythium
Fu = Dusarium Oxy.
Ve = Verticillium dahliae
Ecc = Erwinia carotovora subsp. carotovora
ECA = Erwinia carotovora subsp atroseptica
Res = Residual biocide on tuber immediately after fogging (g/tuber)

TABLE II

| Treatment | Extent of (%) of Affliction In powdery Scab |
|---|---|
| None (control) | 14.2 |
| Fogging In | 1.2 |
| Fogging Out | 2.2 |
| Fogging In & Out | 0 |

TABLE III

| Treatment solution | total* fungi | Rh* | Py* | Fu* | Ve* | Ecc* | Eca* |
|---|---|---|---|---|---|---|---|
| None (control) | $4.1 \times 10^4$ | 17 | 180 | $7 \times 10^3$ | 4 | $3 \times 10^5$ | $4.7 \times 10^5$ |
| A | $1.4 \times 10^4$ | 13 | 62 | $3.7 \times 10^2$ | 4 | $1.5 \times 10^2$ | $1.5 \times 10^3$ |
| B | $1.5 \times 10^3$ | 12 | 7 | $2.5 \times 10^2$ | 2 | 30 | 30 |

*cfu/tuber
RH = Rhizoctonia Solani
Py = Pythium
Fu = Fusarium Oxy.
Ve = *Verticillium Dahliae*
Ecc = *Erwinia carotovora* subsp. *carotovora*
Eca = *Erwinia carotovora* subsp. *atroseptica*

TABLE IV

| Treatment/ Cell No. | total count cfu/tuber | Erwinia cfu/tuber | Fungi cfu/tuber |
|---|---|---|---|
| None (control) | $3 \times 10^6$ | $7 \times 10^3$ | $1 \times 10^2$ |
| 1 | $8 \times 10^4$ | $2 \times 10^3$ | 2 |
| 2 | $1 \times 10^4$ | $2 \times 10^3$ | 2 |
| 3 | $8 \times 10^4$ | $2 \times 10^4$ | $4 \times 10$ |
| 4 | $4 \times 10^4$ | $2 \times 10^3$ | 2 |

TABLE V

| Provenience | Treatment | total count cfu/tuber | Erwinia cfu/tuber | total fungi cfu/tuber |
|---|---|---|---|---|
| Scotland | None | $1 \times 10^8$ | $4 \times 10^4$ | $3 \times 10^3$ |
| Scotland | Fogged | $2 \times 10^5$ | $2 \times 10^3$ | $2 \times 10^2$ |
| Holland | None | $3 \times 10^7$ | $1 \times 10^4$ | $3 \times 10^6$ |
| Holland | Fogged | $3 \times 10^5$ | $3 \times 10^3$ | $4 \times 10^2$ |

I claim:

1. A method for controlling the growth of microorganisms on seed potatoes, comprising providing said seed potatoes in a fogging chamber and applying fog droplets to said seed potatoes, in said chamber, with a fogger, of an effective fungicidal and bactericidal amount of a composition comprising between 10% and 30% by weight of 2,2-dibromo-3-nitrilo-propionamide, between 40% and 70% by weight of dipropylene glycol and between 10% and 30% by weight of water, wherein the diameter of said fog droplets is between about 0.1 and about 30 microns.

2. A method according to claim 1, wherein the ratio between the empty and occupied volume of said fogging chamber is between about zero and about 0.25.

3. A method according to claim 1, wherein the amount of 2,2-dibromo-3-nitrilopropionamide employed for each ton of stored potatoes is between about 0.6 and about 1.2 liter of a 20% solution.

4. A method according to claim 1, wherein the mean diameter of said fog droplets is between about 0.5 and about 4.0 microns.

5. A method according to claim 1, wherein said fogger is a thermal fogger.

* * * * *

UNITED STATES PATENT AND TRADEMARK OFFICE
CERTIFICATE OF CORRECTION

PATENT NO. : 5,169,866
DATED : December 8, 1992
INVENTOR(S) : Barak

It is certified that error appears in the above-indentified patent and that said Letters Patent is hereby corrected as shown below:

Columns 3-4, line 56

Table I, "Fu = Dusarium Oxy." should read --Fu = Fusarium Oxy.--.

Columns, 3-4, line 58,
Table I, "ECA" should read --Eca--.

Column 5, line 8,
Table III, "RH" should read --Rh--.

Signed and Sealed this

Twenty-sixth Day of October, 1993

Attest:

BRUCE LEHMAN

Attesting Officer

Commissioner of Patents and Trademarks